United States Patent [19]

Chu

[11] Patent Number: 5,126,572
[45] Date of Patent: Jun. 30, 1992

[54] TOOTHBUSH HOLDER

[76] Inventor: Tak Y. W. Chu, Lot 232 D.D. 233 Off Clear Water Bay Road, House 10, Ha Yeung New Village, Sai Kung, Kowloon, Hong Kong

[21] Appl. No.: 628,631

[22] Filed: Dec. 12, 1990

[51] Int. Cl.⁵ .................................................. G01N 23/00
[52] U.S. Cl. .................................. 250/455.11; 422/24
[58] Field of Search .................... 250/455.1; 422/24

[56] References Cited

U.S. PATENT DOCUMENTS

| | | | |
|---|---|---|---|
| 2,587,131 | 2/1952 | Ficken | 250/52 |
| 3,954,407 | 5/1976 | Audary et al. | 21/83 |
| 4,088,455 | 5/1978 | Ellis | 250/455.1 |
| 4,625,119 | 11/1986 | Murdock, III | 250/455.1 |
| 4,740,706 | 4/1988 | Murdock, III | 250/455.1 |
| 4,772,795 | 9/1988 | Sakurai et al. | 250/455.1 |
| 4,803,364 | 2/1989 | Ritter | 250/455.1 |
| 4,806,770 | 2/1989 | Hylton et al. | 250/455.1 |
| 4,868,397 | 9/1989 | Tittel | 250/455.1 |
| 4,877,963 | 10/1989 | Min-Jenn | 250/455.1 |
| 4,888,487 | 12/1989 | Ritter | 250/455.1 |
| 4,906,851 | 3/1990 | Beasley et al. | 250/455.1 |
| 4,950,902 | 8/1990 | Ritter | 250/455.1 |
| 4,973,847 | 11/1990 | Lackey et al. | 250/455.1 |
| 4,975,587 | 12/1990 | Min-Jenn | 250/455.1 |

Primary Examiner—Bruce C. Anderson
Attorney, Agent, or Firm—Reese Taylor

[57] ABSTRACT

A personal health care item in the form of a toothbrush holder is provided comprising means to support one or more toothbrushes, and an ultraviolet irradiating light device to treat the brush of any toothbrush mounted within the toothbrush support means and thus kill any germs present within the brush.

11 Claims, 1 Drawing Sheet

TOOTHBRUSH HOLDER

BACKGROUND OF THE INVENTION

This invention relates to toothbrushes and in particular to the hygiene of toothbrushes.

At present, toothbrushes become infected with a small number of germs which initially come from the mouth of the user of the toothbrush. Thereafter, toothbrushes are normally placed within a cup or the like, and thus are very prone to become unhygienic since germs can easily multiply within the brush of the toothbrush and build up to an unhygienic level. This is undesirable, since the user of the toothbrush will during subsequent use, transfer a much greater number of germs into their mouth.

It is accordingly an object of the invention to overcome this problem.

SUMMARY OF THE INVENTION

In accordance with the invention, a personal health care item in the form of a toothbrush holder is provided comprising means to support one or more toothbrushes, and means to treat the brush of any toothbrush mounted within the toothbrush support means and thus kill any germs present within the brush.

Suitably the means for killing germs is an ultraviolet (UV) irradiating light device which is automatically turned on when the brush of a toothbrush is placed within the toothbrush support means.

In particular, the light device in form of a UV light bulb or tube is provided with a timer to control the time the bulb is on (for example 1 to 10 minutes) such that when the brush of the toothbrush is inserted in the toothbrush support means, the UV light bulb is activated for this time, and after the operational time it is turned off.

The support means is preferably positioned adjacent the UV light bulb, and the toothbrush is held in the holder at a distance not more than 5 mm from the UV light.

Suitably the electronic circuitry for the UV light tube is operated by a DC 6 Volt or 9 Volt battery unit and/or a AC adaptor.

The support means suitably includes a mechanical device to hold the toothbrush, and a one way triggering switch to detect the toothbrush pushing into the holder and turn on the UV light device.

Suitably th exterior of the toothbrush holder includes one or more animal or animal head shapes, each of which have a mouth through which the head of a toothbrush can be positioned into the support means.

Suitably, four animal images or heads are mounted on the holder as a cover such that they are interchangeable.

BRIEF DESCRIPTION OF THE DRAWINGS

The invention will now be described by way of example with reference to the accompanying drawings in which.

DESCRIPTION OF THE PREFERRED EMBODIMENTS

Figure 1:
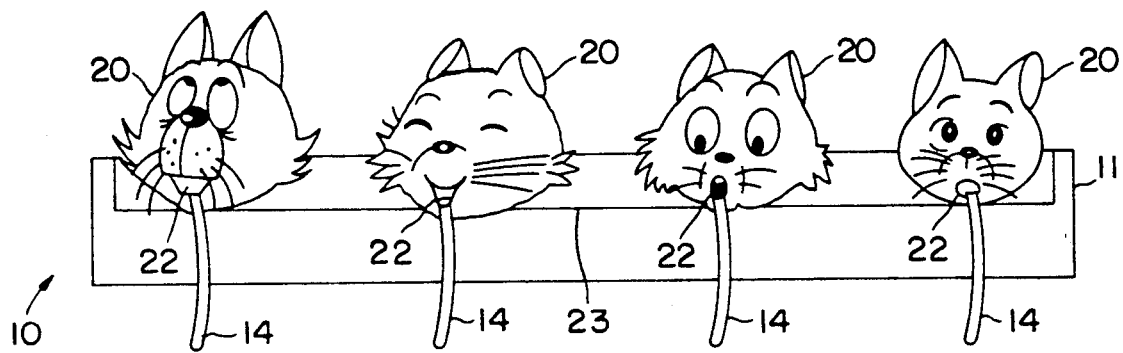
FIG. 1 shows a toothbrush holder having a cover for four toothbrush holders in the form of animals heads.
Figure 2:
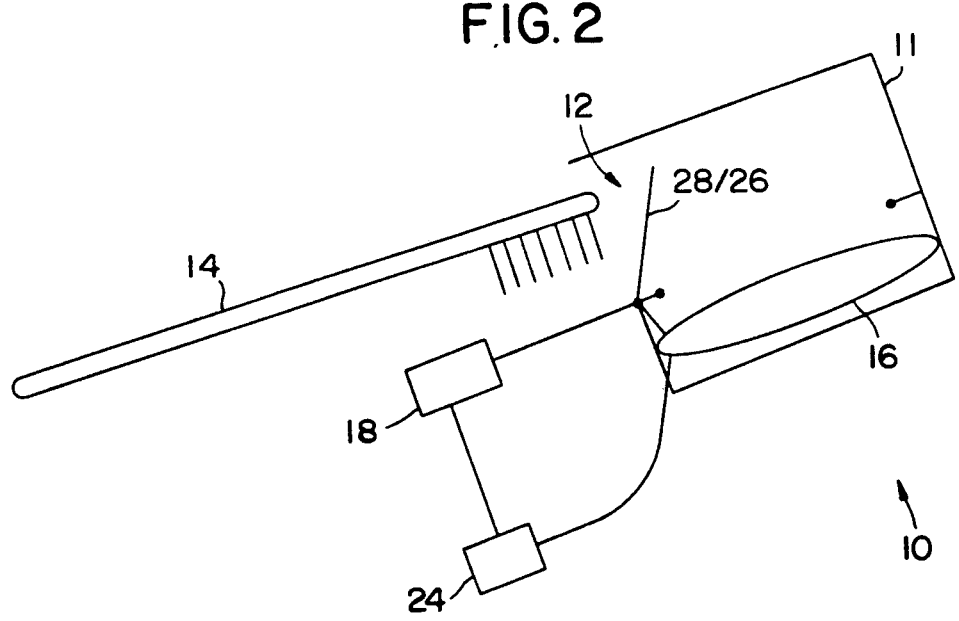
FIG. 2 shows a schematic diagram of a cross-sectional portion of the holder shown in FIG. 1.

A toothbrush holder 10 is provided with a housing 11 comprising means 12 to support one or more toothbrushes 14, and means 16 to treat by irradiation the brush of the toothbrush placed within the toothbrush support means and thus kill any germs present within the brush.

The means for killing germs is a UV light device 16 which is automatically turned on when the brush of a toothbrush is placed within the toothbrush support means.

In particular, a UV light bulb is provided with a timer 18 to control the time the bulb is on (for example 1 to 10 minutes) such that when the brush of the toothbrush is inserted in the toothbrush support means, the UV light bulb is activated for this time, and after the operational time it is turned off.

The support means 12 is positioned adjacent the UV light bulb 16, and the toothbrush is held in the holder at a distance not more than 5 mm from the UV light.

Suitably the electronic circuitry for the UV light tube is operated by a DC 6 Volt or 9 Volt battery unit 24 and/or a AC adaptor.

The support means 12 comprises a mechanical device 26 to hold the toothbrush within the housing 11. A one way triggering switch 28 is also provided to detect the toothbrush pushing into the holder and turn on the UV light 16. In particular, a pivoting flap 28/26 is provided which acts as both the mechanical device to hold the toothbrush and the one way triggering switch.

The toothbrush holder 10 includes four animal head shaped 20 each of which have a mouth 22 through which the head of a toothbrush can be positioned into the support means. The four animal images or heads are mounted on the holder as a cover 23 so that they can be interchangeable.

The four animal heads are also shown in the form of a family of four, namely an image of the father, mother and two children.

A latitude of modification, change and substitution is intended in the foregoing disclosure and in some instances some features of the invention will be employed without a corresponding use of other features. Accordingly it is appropriate that the appended claims be construed broadly and in a manner consistent with the spirit and scope of the invention herein.

I claim:

1. A personal health care item in the form of a toothbrush holder, comprising: support means for supporting at least one toothbrush; means for treating the brush of a toothbrush received within the support means and thus kill any germs present within the brush; and means for activating said means for treating as a toothbrush is inserted into said support means.

2. The personal health care item as claimed in claim 1 wherein the means for treating is an ultraviolet irradiating light device.

3. The personal health care item as claimed in claim 2 wherein the light device is a UV light bulb.

4. The personal health care item as claimed in claim 2 wherein said support means and said means for activating comprise a single, pivoted flap and switch.

5. The personal health care item as claimed in claim 1 wherein the means for treating is interconnected with a timer to control the time said means is activated.

6. The personal health care item as claimed in claim 1 wherein the support means is positioned adjacent the means for treating.

7. The personal health care item as claimed in claim 1 wherein the electronic circuitry for the means for treating is operated by a battery unit.

8. The personal health care item as claimed in claim 1 including a one way triggering switch to detect a toothbrush entering into the holder and activate the means for treating.

9. The personal health care item as claimed in claim 1 wherein the exterior of the toothbrush holder includes at least one animal shape; said animal shape having a mouth through which the head of a toothbrush can be positioned into the support means.

10. The personal health care item as claimed in claim 9 wherein said animal shapes are mounted on the holder as a cover therefor.

11. A personal health care item in the form of a toothbrush holder, comprising: a housing; support means carried by said housing for supporting a toothbrush within said housing; means for treating the brush of a toothbrush received within said support means and thus kill any germs present within the brush; said support means including a combined, pivoted flap and switch swingable toward the interior of said housing to support the toothbrush and activate said means for treating as the toothbrush is inserted into said support means.

* * * * *